United States Patent [19]
Köttig

[11] Patent Number: 5,776,077
[45] Date of Patent: Jul. 7, 1998

[54] APPARATUS FOR MEASURING URINE OUTPUT

[75] Inventor: Thomas Köttig, Neckargemünd, Germany

[73] Assignee: Walter Sarstedt Gerate und Verbrauchs-Material for Medizin und Wissenschaft, Numbrecht, Germany

[21] Appl. No.: 773,231

[22] Filed: Dec. 23, 1996

[30] Foreign Application Priority Data

Dec. 23, 1995 [DE] Germany .................. 195 48 678.1

[51] Int. Cl.$^6$ .................................................. A61B 5/00
[52] U.S. Cl. ........................ 600/573; 604/349; 600/580
[58] Field of Search ........................ 604/349; 600/573, 600/574, 584, 581, 575

[56] References Cited

U.S. PATENT DOCUMENTS 4,846,816  7/1989  Manfredi .................. 604/349
5,618,277  4/1997  Goulter .................... 604/349

FOREIGN PATENT DOCUMENTS 4338687  12/1993  Germany .................. 600/573

Primary Examiner—Robert A. Clarke
Attorney, Agent, or Firm—Herbert Dubno; Andrew Wilford

[57] ABSTRACT

A urine-output measuring apparatus has a catheter adapted to be inserted in a patient and having an outer end, a stationarily mounted flow device having an input connected to the outer end of the catheter and an output, a highly flexible tube having an input end connected to the output of the flow device and an output end, and an elongated urine-collection bag connected to the output end of the flexible tube. A relatively incompressible but flexible and elongated element of noncircular section is loosely received in the tube and extends generally a full length of the tube between its ends.

4 Claims, 1 Drawing Sheet

APPARATUS FOR MEASURING URINE OUTPUT

FIELD OF THE INVENTION

The present invention relates to a urine measuring apparatus. More particularly this invention concerns such an apparatus used to measure urine output from a catheterized patient.

BACKGROUND OF THE INVENTION

It is standard in intensive-care units and the like to closely monitor the fluid outputs, particularly the urine output, of a patient, in particular one being supplied fluids intravenously. The ratio of fluid intake to fluid output is an important measure of the condition of important physiological processes, particularly of kidney function.

Accordingly it is standard to catheterize a patient on an intravenous feed. The catheter, which is a thin flexible tube passed through the urethra directly into the patient's bladder, has its outer end connected to an apparatus such as described in German patent document 4,338,687. This apparatus has a vessel, normally a bag that is used to collect the urine and that is hung from a device that tracks its weight with respect to time to record the patient's urine output.

In order to prevent any backflow which could lead to infection the catheter opens into a flow device constituted by a drip chamber whose outlet is provided with a check valve. A highly flexible latex tube leads from this check valve to the collection bag so that this tube does not significantly affect the weight of the bag. Any blockage or backup will be caught by the check valve and the drip chamber so flowback to the patient is largely avoided. As a rule such a device is hung directly on the patient's bed, on the side at a level well below the patient as the catheter relies on gravity flow to work. Connecting the catheter to the solidly anchored drip chamber provides strain relief for the system, so that even if the catheter itself is tensioned, the weight of the urine-holding bag is unaffected.

A common problem occurs when a nurse, other attendant, or even the patient physically disturbs the measuring apparatus. The catheter itself is of small diameter and relatively incompressible, but the tube connected to the bag is very limp and flexible, so that as described above it does not affect the weight of the bag, and it can easily get bent or kinked. When this happens flow through it is blocked and backs up. Even though the check valve and drip chamber normally prevent such a backup from reaching back to the patient before quite some time has elapsed, such a blockage can falsify the readings. When the kink is straightened out the trapped urine flows into the bag, so that the monitoring equipment will record a sudden spike in bag weight that does not represent the patient's actual urine output, substantially invalidating the readings from a short-term point of view.

Accordingly it has been suggested in German patent document 3,544,031 to provide an elastic sleeve to protect the tube from the check valve to the urine bag. This sleeve is supported on special arms with the urine bag. While relatively effective, this extra equipment is relatively bulky and adds considerably to the cost of the device.

OBJECTS OF THE INVENTION

It is therefore an object of the present invention to provide an improved apparatus for measuring urine output from a catheterized patient.

Another object is the provision of such an improved apparatus for measuring urine output from a catheterized patient which overcomes the above-given disadvantages, that is which is relatively simple but which surely prevents any kinking and blockages of the tube connected directly to the urine-collection bag.

SUMMARY OF THE INVENTION

A urine-output measuring apparatus has according to the invention a catheter adapted to be inserted in a patient and having an outer end, a stationarily mounted flow device having an input connected to the outer end of the catheter and an output, a highly flexible tube having an input end connected to the output of the flow device and an output end, and an elongated urine-collection bag connected to the output end of the flexible tube. According to the invention a relatively incompressible but flexible and elongated element of noncircular section is loosely received in the tube and extends generally a full length of the tube between its ends.

Thus even if the tube is kinked or bent, the element will hold it open enough for flow to continue through it. Thus the bag will continue to fill under circumstances where all flow into it would be cut off in prior-art systems. The cross-sectional shape of the element is such that it is impossible for the inner wall of the tube to seat against it in all-around engagement, ensuring flow under all conditions.

According to the invention the flow device is a drip chamber and a check valve. In addition means is provided for securing the flow device to a bed holding the patient and for suspending the bag from the bed adjacent the flow device.

The elongated element according to the invention is formed as a string of beads of noncircular section. It can also be a helical spring-like member or formed with a helical groove.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
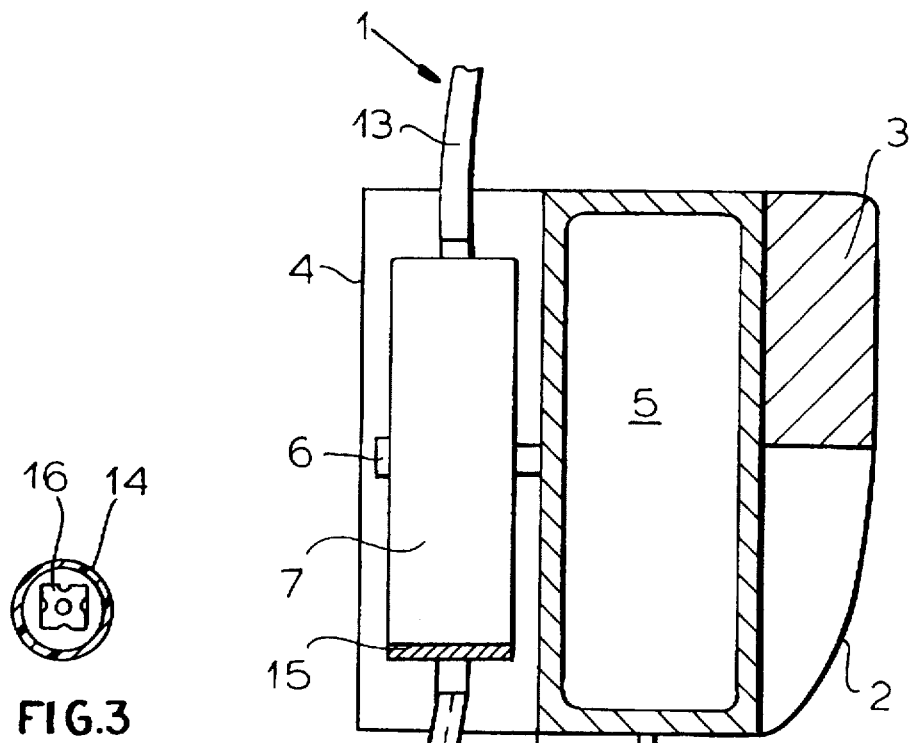
FIG. 1 is a partly sectional and schematic side view of the system of this invention.

As seen in FIG. 1 an apparatus 1 for measuring urine output has a housing 4 secured by a strap 2 to a bed frame 3 on which is supported an unillustrated patient whose urine output is being monitored. The housing 4 accommodates a circuit-display block 5 not shown in detail and has a clip 6 to which is secured a flow device comprised of a conventional drip chamber 7 and check valve 15.

A standard catheter tube 13 has its output end secured to the top inlet of the drip chamber 7 and the check valve 15 constituting the outlet of this chamber 7 is connected via a very flexible latex tube 14 to a urine-collection bag 12 having a drain valve 11. Hanger fittings 10 and a weight-detecting device 9 suspend the bag 12 from the housing 4. A cable 8 connects the weight-detecting device 9 to the electronics block 5 so that can continuously monitor the weight of the bag 12.

Figure 3:
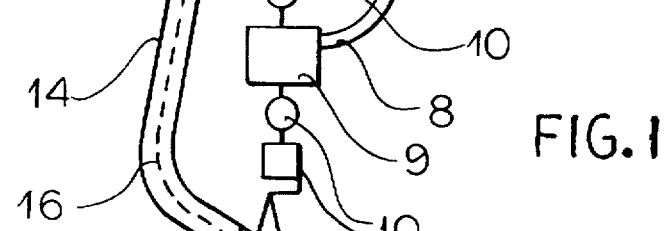
FIG. 3 is a section taken along line III—III of FIG. 2.
Figure 2:
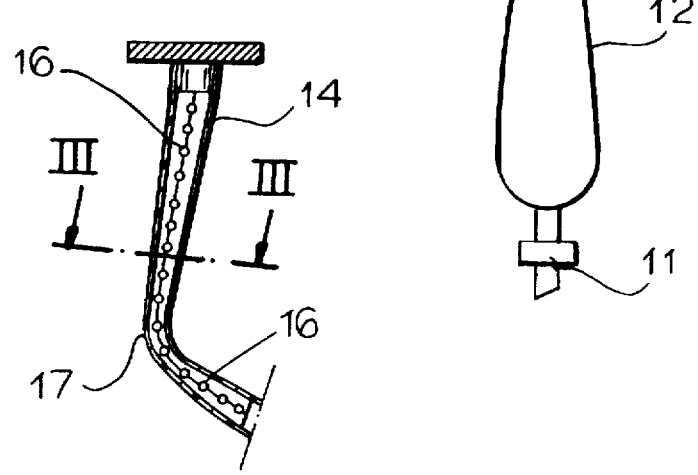
FIG. 2 is a detailed sectional view of the invention with the tube kinked.

According to the invention the tube 16 is provided internally with an elongated element 16 formed as shown in FIGS. 2 and 3 as a series of square-section beads each of whose faces is formed with a longitudinal groove. This element 16 extends coaxially the full length of the tube 14. The chain element 16 is very flexible, like the tube 14 and formed of a biologically inert plastic.

If the tube 14 is kinked as shown at 17, the beads of the element 16 will ensure that enough flow cross section remains open to prevent urine from backing up in the system.

I claim:

1. In a urine-output measuring apparatus comprising:

a catheter adapted to be inserted in a patient and having an outer end;

a stationarily mounted flow device having an input connected to the outer end of the catheter and an output;

a highly flexible tube having an input end connected to the output of the flow device and an output end; and an elongated urine-collection bag connected to the output end of the flexible tube, the improvement comprising a relatively incompressible but flexible and elongated element of noncircular section loosely received in the tube and extending generally a full length of the tube between its ends.

2. The improved urine-output measuring apparatus defined in claim 1 wherein the flow device is a drip chamber and a check valve.

3. The improved urine-output measuring apparatus defined in claim 1, further comprising means for securing the flow device to a bed holding the patient and for suspending the bag from the bed adjacent the flow device.

4. The improved urine-output measuring apparatus defined in claim 1 wherein the elongated element is formed as a string of beads of noncircular section.

* * * * *